United States Patent [19]

Adair

[11] 4,284,079
[45] Aug. 18, 1981

[54] METHOD FOR APPLYING A MALE INCONTINENCE DEVICE

[76] Inventor: Edwin L. Adair, 191 E. Orchard, Littleton, Colo. 80123

[21] Appl. No.: 52,865

[22] Filed: Jun. 28, 1979

[51] Int. Cl.³ .............................................. A61F 5/44
[52] U.S. Cl. .................................. 128/295; 128/760; 128/767
[58] Field of Search ............... 128/294, 295, 760, 767; 4/144.1, 144.2, 144.3; 138/99; 285/293, 423, 373, 419, DIG. 16

[56] References Cited

U.S. PATENT DOCUMENTS

| | | | |
|---|---|---|---|
| 2,305,453 | 12/1942 | Martos | 128/156 |
| 2,448,938 | 9/1948 | Waync | 128/294 |
| 3,037,508 | 6/1962 | Friedman | 128/294 |
| 3,677,225 | 7/1972 | Czirely | 128/294 |
| 3,788,324 | 1/1974 | Lim | 128/295 |
| 3,951,141 | 4/1976 | Kopelowicz | 128/294 |
| 4,119,094 | 10/1978 | Micklus et al. | 128/294 |
| 4,187,851 | 2/1980 | Hausor | 128/295 |
| 4,202,335 | 5/1980 | Gold | 128/295 |

Primary Examiner—Robert W. Michell
Assistant Examiner—J. L. Kruter
Attorney, Agent, or Firm—Sheridan, Ross, Fields & McIntosh

[57] ABSTRACT

A male incontinence device is provided including a flexible, thin sheet including a rim positioned along the outer edge of the sheet and a covering layer overlying the space within the rim. The rim comprises a first surface and a second surface with a foam layer connected therebetween. The rim also includes an inner and outer periphery. Portions of the inner periphery are positioned in the coronal sulcus of the penis. A drainage tube is placed adjacent the urethra opening. Portions of the rim, together with the covering layer, are folded over the head of the penis. Portions of the rim are joined together along the first surface thereof to tightly secure the device and drainage tube to the penis so that the escape of urine, other than through the drainage tube, is greatly minimized.

2 Claims, 8 Drawing Figures

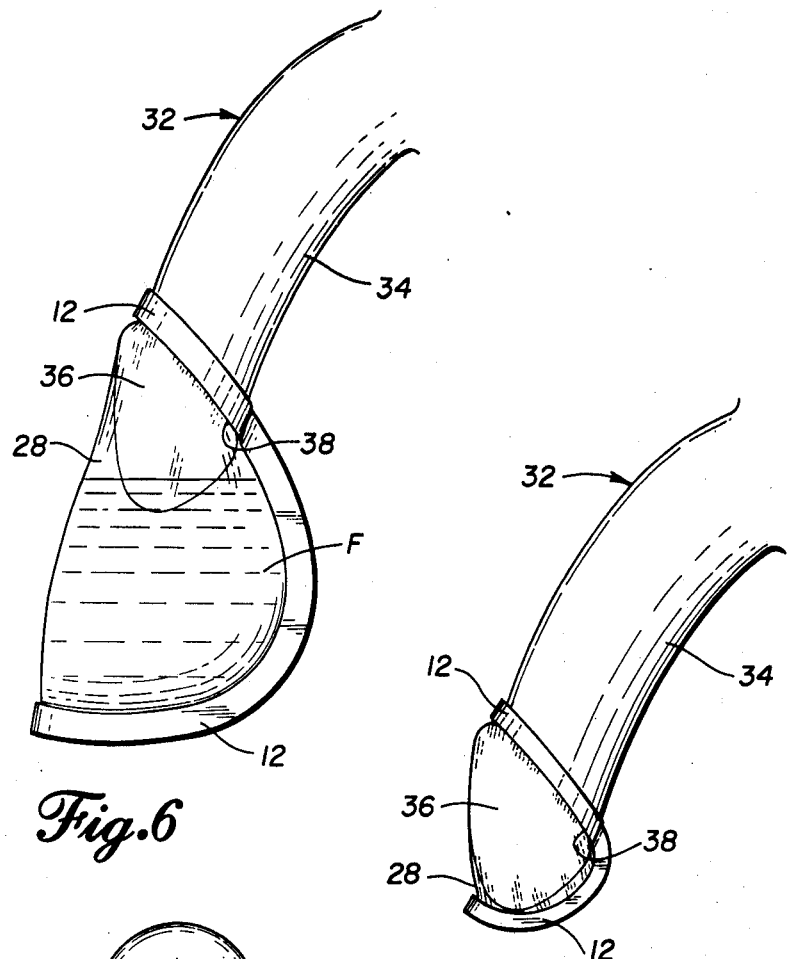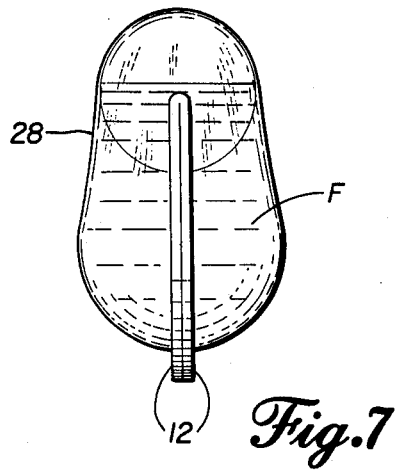

METHOD FOR APPLYING A MALE INCONTINENCE DEVICE

FIELD OF INVENTION

This invention relates to male incontinence devies and, in particular, to a male incontinence device fastenable along the coronal sulcus of the penis of the male.

BACKGROUND ART

Various male incontinence devices are disclosed. Many of these devices use a tube or a condom-shaped piece to surround the penis. In U.S. Pat. Nos. 3,835,857 and 3,863,638 to Rogers, II, et al., a sheath is integrally joined to a conical portion to surround the penis head and portions of the penis shaft. In U.S. Pat. No. 2,789,560 to Weimer, a cap having an opening and a nozzle inserted into the opening is disclosed. The cap surrounds the penis head while a sheath is connected to the cap and the penis. Infant urine collectors utilizing foam pads underlying adhesive surfaces for attachment near the penis are shown in U.S. Pat. No. 3,340,876 to Hill and U.S. Pat. No. 3,406,690 to Iget, et al. Many of the condom-like devices are irritating to the penile skin and cannot be worn for long periods of time because of the increasing discomfort. Occasionally, these devices do impede some of the blood flow through the penis. Male incontinence devices are also of a type which use a leg bag collector in combination with a condom over the penis and a drainage tube attached therebetween. Often times, the urine contacts the penile skin causing severe excoriation and maceration to the penis.

DISCLOSURE OF THE INVENTION

In accordance with this invention, a male incontinence device and method for applying the device to the penis is provided. The device includes a generally flat, thin sheet or film having a rim. The rim has a first surface and a second surface with a covering layer attached to the second surface. Portions of the rim are seated in the coronal sulcus of the penis. Remaining portions of the rim are joined together around the head of the penis while a drainage tube is held in the device adjacent the urethra to receive urine.

More particularly, a device is provided to be worn by a male patient who is unable to control his urination, and also has application as a condom. The device includes a ring having a first and a second adhesive layer with a layer or foam therebetween. A thin, covering layer covers the space formed within the ring and is attached to the second adhesive layer which overlies a second surface. A first surface is coated with the first adhesive layer overlying which is a release backing. In operation, the release backing is removed and portions of the ring are seated in the coronal sulcus which is located between the penis head and the shaft of the penis. An end of a drainage tube is positioned adjacent the urethra opening. Subsequently, the device is folded so that remaining portions of the ring are joined together along the second adhesive layer thereby securing the device and the drainage tube to the penis. Alternatively, the device may be held on the penis without the drainage tube. In such an application, the device is of a larger size to hold the fluid therein. When the device acts as a condom without the drainage tube connected, it is of a relatively smaller size to fit about the penis head and block the passage of the male sperm.

In light of the foregoing, a number of worthwhile advantages are readily apparent. An incontinence device is provided to prevent the passage of fluid therethrough while connected adjacent the head of the penis. In a first embodiment, the device holds a drainage tube adjacent the urethra opening to receive the urine and carry it to a receptacle. In a second embodiment, the device itself holds the urine since the discharge tube is not attached. This is particularly useful when fluid leakage from the urethra is minimal so that, upon becoming filled with fluid over a period of time, the device is discarded and replaced. In a third embodiment, the device acts as a condom to prevent the passage of male sperm. Generally, the device is tightly secured to the penis along the coronal sulcus so that impairment of the blood supply to the penis head is greatly minimized. The device provides a tight seal to prevent the passage of urine onto the penile skin thereby virtually eliminating the excoriation and maceration thereof. Discomfort to the wearer of the incontinence device over a long period of time is also greatly minimized. Furthermore, the device is easily manufactured while being quickly and efficiently attached to the penis. Additionally, the device of this invention is readily disposable since it is inexpensively made. Additional advantages of this invention will become readily apparent when taken in conjunction with the accompanying drawings.

BRIEF DESCRIPTION OF THE DRAWINGS

FIG. 6 is a perspective view of the incontinence device attached at the coronal sulcus showing fluid contained therein;

FIG. 7 is a frontal view of the incontinence device showing details of the incontinence device attached to the penis and holding fluid therein; and FIG. 8 is a perspective view of the incontinence device showing the device acting as a condom.

DESCRIPTION OF THE PREFERRED EMBODIMENT

Figure 1:
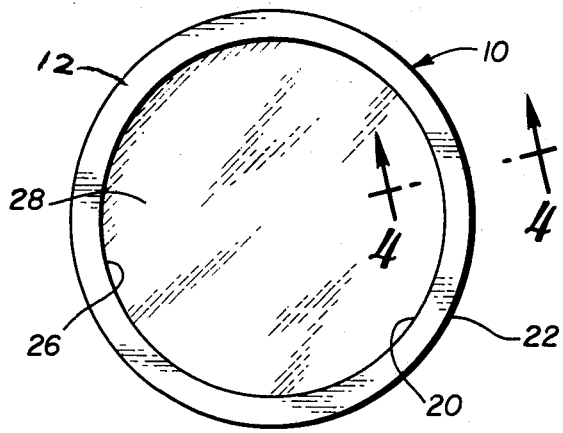
FIG. 1 is a top plan view of the incontinence device having a generally circular shape.
Figure 4:
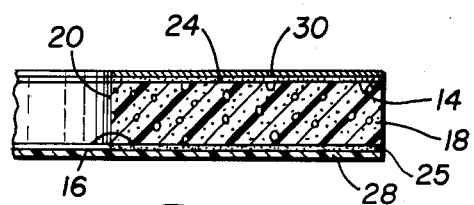
FIG. 4 is an enlarged, fragmentary, lateral section, taken along line 4—4 of FIG. 1, showing details of the rim.

In accordance with the present invention, a device is provided which is of benefit to a male unable to control the flow of urine from his urethral passage as well as for use as a condom. As depicted in FIG. 1, a generally thin, flat, flexible, circular sheet or film 10 is provided. Sheet 10 includes a rim or peripheral edge 12 in the form of a ring provided along the edge of the sheet 10. Rim 12 includes a first surface 14 and a second surface 16. Interposed between first surface 14 and second surface 16 is a foam layer 18, as shown in FIG. 4. Foam layer 18 is preferably made of a soft, closed cell foam having a thickness of 1/16 inch to ⅛ inch. Rim 12 further includes an inner or first periphery 20 and an outer or second periphery 22. A first adhesive layer 24 is applied over first surface 14 while a second adhesive layer 25 is applied over second surface 16. A space 26 is formed within the confines of inner periphery 20 of rim 12. A covering layer 28 is contiguously connected to the second adhesive layer 25 and extends over space 26. Covering layer 28 preferably is made of a thin, transparent sheet of plastic which is elastic, such as vinyl or polyester. A release backing 30 is provided over the first adhesive layer 24 of rim 12 to protect the adhesive quality thereof until the device is ready for use.

Figure 2:
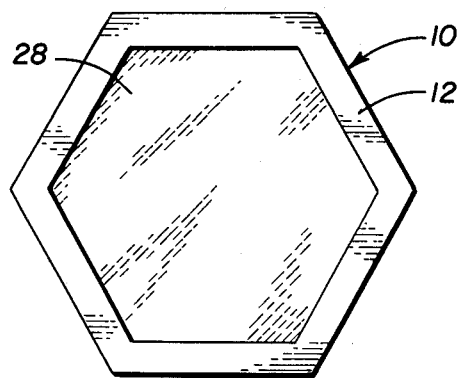
FIG. 2 is a top plan view of the incontinence device having a generally hexagonal shape.

Although FIG. 1 shows the shape of the sheet 10 to be generally circular, it is understood that many other shapes are equally feasible to act as an incontinence device as described herein. A generally hexagonal sheet 10 can also be provided, as illustrated in FIG. 2. Similar to the circular sheet, hexagonal sheet 10 includes a rim 12 having the same structure as shown in FIG. 4 and a covering layer 28. Furthermore, sheet 10 may have an oval, octagonal or any other configuration which is adaptable for the application which is to be subsequently described in detail.

Figure 3:
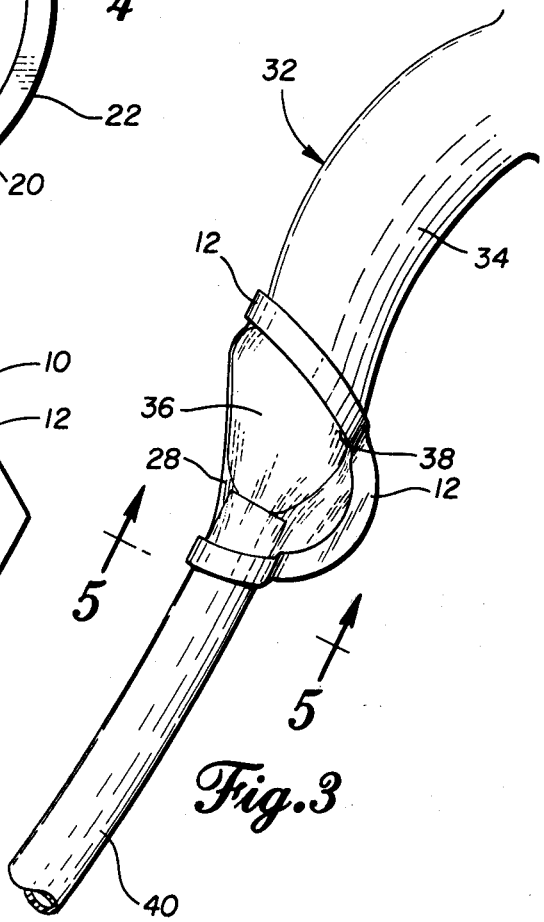
FIG. 3 is a perspective view of the incontinence device attached at the coronal sulcus with a drainage tube extending therefrom.

The application of the male incontinence device with a drainge tube is best seen in FIG. 3. A penis 32 is illustrated which anatomically includes a shaft 34 and a head or glans 36. A depression 38, which is defined as the coronal sulcus, is formed on the shaft 34 and is located immediately adjacent the head 36 between the shaft 34 and the head 36. The depression 38 completely encircles the penis and is present in both circumcised and uncircumcised males. Of significance to the application of this invention is the fact that the blood supply to the shaft 34 of the penis 32 is virtually separate from the blood supply to the head 36. Consequently, a relatively tight constriction of the coronal sulcus 38 does not restrict the vascular supply to the head of the penis. This conclusion of minimal or no effect on blood supply to the penis head when a relatively tight constriction is imposed on the coronal sulcus has been verified through experimentation. Furthermore, this conclusion has been supported by the effects of a condition naturally occuring in uncircumcised males, medically termed paraphynosis. Paraphynosis is the retraction of an already constricted foreskin to the coronal sulcus. The band of constriction in the foreskin cannot be dislodged and the foreskin becomes markedly edematous, thereby losing its usual appearance and can become gangrenous. When this condition has occurred, it was noticed that the penis head essentially maintained its usual appearance and fitness as the blood supply was virtually unimpeded thereto.

Figure 5:
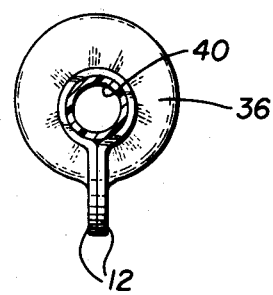
FIG. 5 is a lateral section, taken along line 5—5 of FIG. 3, showing details of the incontinence device attached to the penis with a drainage tube extending therefrom.

In applying the incontinence device of this invention the release backing 30 is initially removed from the first surface 14 of rim 12 to expose first adhesive layer 24. The sheet 10 is placed over a first or front side of the penis 32, which is the side of the penis opposite that side adjacent the scrotum of the male. Portions of the inner periphery 20 of rim 12 are seated in the coronal sulcus 38 while those portions of the rim 12 laterally adjacent the seating portions of inner periphery 20 are adhesively connected to the shaft 34. A drainage tube 40 is placed adjacent the urethra opening. The sheet 10 is then folded around the head 36 of the penis 32 in the direction of the underside of the penis towards the scrotum so that portions of rim 12 adhesively contact each other, as shown in FIG. 5. The sheet 10 is thereby maintained on the penis head 36 and the drainage tube 40 held therein. Conveniently, a collector (not shown) is attached to the end of the drainage tube 40, opposite the end adjacent the urethra opening, to catch the urine flowing through drainage tube 40. The sheet 10 is of a size to comfortably but sealingly cover the penis head 36 so that urine or fluid cannot escape from the urethra opening except through drainage tube 40.

Although the incontinence device has been described for use with a drainage tube 40, FIGS. 6 and 7 show another embodiment in which the device is attached to the penis without the drainage tube 40. The embodiment of FIGS. 6 and 7 is virtually identical to the device previously described except that the incontinence device is relatively larger in size to accommodate the fluid F passing from the urethra. Consequently, the device can be used to trap fluid over a period of time when the leakage from the urethra opening is minimal. After becoming filled with fluid, the device is discarded and replaced.

A third embodiment of the device is depicted in FIG. 8. Again, the embodiment of FIG. 8 is virtually identical to the device previously described except that is is relatively smaller in size to fit closely about the penis head. The device acts as a condom to trap sperm with the rim 12 formed of a very soft foam and the covering layer 28 made of a very soft and thin polypropylene material.

Based on the foregoing description, a number of worthwhile advantages for the present invention are readily apparent. A device is provided which is tightly and sealingly applied to the penis head to aid an incontinent male as well as for use as a condom. The device is tightly seated in the coronal sulcus so that the blood supply to the head of the penis is minimally impeded. The incontinence device may be used together with a drainage tube to deliver urine escaping the urethra to a receptacle or the device may be used by itself to trap and hold urine which passes from the urethra in small amounts over a period of time. Furthermore, the tight seal about the penis head greatly minimizes the escape of urine except through the drainage tube thereby substantially minimizing the excoriation and maceration of the penis. The incontinent device is quickly and efficiently applied and is inexpensively made so that it can be readily disposed of. The device is also lightweight and of simple construction so that it is comfortable to the wearer. In addition, the device has application as a condom wherein it is attached closely about the penis head to prevent the passage of sperm therethrough.

This invention has been described in detail with reference to a plurality of embodiments thereof, but it will be understood that various other modifications can be effected within the spirit and scope of this invention.

I claim:

1. A method for attaching an incontinence device to the penis of a male using a discharge tube therewith, comprising the steps of:

providing a discharge tube and a flexible planar sheet having a closed circumferentially planar rim attached in an overlying relationship to said planar sheet with an inner periphery and an outer periphery;

seating said inner periphery of said rim immediately adjacent the coronal sulcus of the penis while said outer periphery of said rim surrounds the shaft of the penis;

placing an end of the discharge tube adjacent the penis head;

folding said sheet around the penis head and the end of the drainage tube;

forming secured portions and unsecured portions of said rim; and connecting the unsecured portions of said rim together along the entire width of said rim portions, the width being defined as the distance between said outer periphery and said inner periphery, to tightly secure the device and the discharge tube to the penis to greatly minimize the escape of fluid from the penis except through the discharge tube.

2. A method adapted for attaching a device to the penis of a male, comprising the steps of:

providing a single, flexible, substantially planar sheet impervious to the passage of fluid having a closed circumferentially planar rim attached in an overlying relationship to said planar sheet, said rim having an inner periphery and an outer periphery;

folding said sheet to surround the penis head;

forming secured portions and unsecured portions of said rim; and connecting the unsecured portions of said rim together along the entire width of said rim portions, the width being defined as the distance between said outer periphery and said inner periphery, to tightly secure the device to the penis so that fluid escaping the urethra opening of the penis is contained in the device.

* * * * *